United States Patent [19]

Shmidt et al.

[11] Patent Number: 5,131,994
[45] Date of Patent: Jul. 21, 1992

[54] ELECTROPHORESIS METHOD AND APPARATUS

[76] Inventors: Joseph L. Shmidt, 40 Brighton 1st Rd., Apt. 15D, Brooklyn, N.Y. 11235; Huk Y. Cheh, 29-06 214 St., Bayside, N.Y. 11360

[21] Appl. No.: 628,595

[22] Filed: Dec. 17, 1990

[51] Int. Cl.$^5$ ............... B01D 57/02; B01D 61/42; C25D 13/00
[52] U.S. Cl. ............... 204/180.1; 204/299 R; 204/182.1
[58] Field of Search ............... 204/180.1, 299 R

[56] References Cited

U.S. PATENT DOCUMENTS 4,787,963  11/1988  MacConnell ............... 204/180.1
4,849,078  7/1989  Love et al. ............... 204/180.1

Primary Examiner—John Niebling
Assistant Examiner—Caroline Koestner

[57] ABSTRACT

The present invention relates to a method and apparatus for effecting an electrophoretic separation of charged particles. A fractionation chamber comprising a semipermeable membrane is used wherein a transmembrane force holds the particles to be separated against the membrane surface while a voltage gradient is applied to separate the particles.

11 Claims, 1 Drawing Sheet

ELECTROPHORESIS METHOD AND APPARATUS

The present invention relates to an electrophoretic method for separating a mixture of charged particles and an apparatus for effecting the same. In particular, the invention relates to electrophoresis along a membrane surface having transmembrane forces applied therethrough.

Electrophoretic fractionations are generally performed in a gel or in a stream of free flowing electrolyte carrier. A typical gel electrophoresis technique comprises the electromigration of a small sample of a protein mixture through a slab of a porous gel matrix under an applied electric field. The individual components of the mixture generally each have a different electrophoretic mobility such that they all move at different velocities under the applied field whereby separation occurs over time. The gel is used to reduce thermal convection which arises from heat generated by the electric current which flows between the electrodes. The gel also serves as a molecular sieve in that a "drag" effect arises as the larger species try to move through the viscous media. Although gel electrophoresis is a common technique for analyzing different macromolecules, it can not be used to separate organelles and whole cells due to restrictions on the motion of such large species through a gel. An additional drawback of gel electrophoresis is that recovery of the fractionated species from the gel is a difficult and time consuming operation.

Free flow electrophoresis is more amenable for fractionating cells and macromolecules, i.e. procaryotic and eucaryotic cells, red blood cells and lymphocytes, cell organelles, viruses, chromosomes, inclusion bodies and membrane proteins. Extensive research efforts have been devoted to continuous free flow electrophoresis but its use is hampered by poor resolution and complexity of the apparatus. Poor resolution is caused by several factors including a phenomena called crescent flow. Crescent flow arises from a parabolic velocity profile of the fluid carrier whereby the fluid in the center of the stream flows faster than the fluid near the walls of the fractionation chamber. This results in uneven residence time for dispersed species. Electroosmotic flow and thermally induced convection also contribute to the poor resolution.

A relatively new analytical electrophoretic technique is capillary electrophoresis. According to this method the charged species are fractionated along the axis of glass capillaries having a narrow bore. The capillaries may or may not be filled with a gel. This method is characterized by very small sample volumes and relatively short detection times. Further, this method is limited by the complexity and precision of the associated apparatus, the need for high resolution instrumentation, and by the presence of electroosmotic flows which detrimentally affects the resolution of fractionated species.

It is an object of the present invention to provides a method and apparatus for the fractionation of charged particles, including cell-sized charged particles, with high resolution.

It is an additional object of the present invention to provide a method and apparatus for the fractionation of charged particles which combines the simplicity of gel electrophoresis with the gentleness and high sample recovery of free flow electrophoresis.

The features and advantages of the present invention are discussed below in greater detail with reference to the accompanying Figures in which.

In accordance with the present invention, an electrophoresis method for fractionating charged particles comprises applying a mixture of charged particles onto a membrane surface located in a fractionation chamber filled with a conductive electrolyte solution and then applying a transmembrane force perpendicular to the membrane to hold the particles against the membrane surface. An electric field is then applied parallel to the membrane surface such that the particles migrate according to their electrophoretic mobilities. whereby separation occurs. The magnitude of the transmembrane force should not be so great so as to retard migration but should be great enough so as to prevent dispersion of the particles due to convection.

An apparatus for carrying out the above described method comprises a fractionation chamber comprising a membrane and sample introduction means for applying a mixture of charged particles onto a portion of the membrane surface. Means for applying a transmembrane force is provided for holding the particles against the membrane surface and electric field means is provided for generating an electric field gradient parallel to the membrane surface.

The present invention does away with the need for a gel matrix to minimize dispersion due to convection since the transmembrane force retards dispersion of the particles. The transmembrane force can be any force which interacts with some physical property of the particles to hold them in place. In a preferred embodiment the membrane is a semipermeable structure having pores at least several times smaller than the average particle size of the particles to be separated. A flow of electrolyte through the membrane creates a force in a boundary layer at the membrane surface which holds the particles gently against the membrane surface. However, it is not inconceivable that other forces such as magnetic or gravitational forces could be used for particular types of particles and such embodiments are intended to be within the scope of the present invention as claimed.

The sample size in membrane surface electrophoresis as described herein is relatively small because fractionation occurs mainly in a thin layer at the membrane surface. This technique is especially favorable for separation of larger cells with low diffusion coefficients without the restriction on particle size that is imposed by the use of gel techniques.

Figure 1:
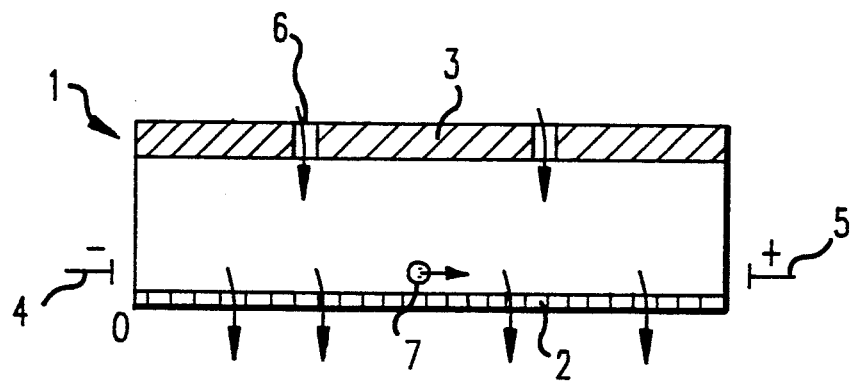
FIG. 1 is a schematic representation of a fractionation chamber in accordance with the present invention.

The method of the present invention will be more fully described in reference to the schematic representation of a fractionation chamber shown in FIG. 1. FIG. 1 shows a rectangular fractionation chamber 1 having semipermeable membrane 2 located in the bottom thereof. Negative electrode 4 and positive electrode 5 are located at opposite sides of chamber 1. A mixture of the charged particles is applied locally onto the membrane surface. If the particles are all positively charged they are preferably placed on the membrane surface near positive electrode 5 or if all negatively charged they are placed on the membrane surface near negative electrode 4. A mixture of positively charged and negatively charged particles would be placed near the middle. It is important that the sample is delivered onto a confined area of the surface so that all of the particles begin at roughly the same starting point when the electric field is applied.

A transmembrane force is applied to hold the particles at the membrane surface. In a preferred embodiment a pressure differential is created between the carrier electrolyte above and below membrane 2 so that the pressure is greater above membrane 2 where the particles are located. Since membrane 2 is permeable to the carrier electrolyte there is a flow through the membrane, driven by the pressure differential, which creates the desired force to hold the particles in place. Throughout the process electrolyte is supplied from a reservoir through suitable openings 6 and into chamber 1 while electrolyte is collected from below membrane 2 through suitable collection means. Alternatively, electrolyte could be circulated from below membrane 2 back into the reservoirs which feed chamber 1.

An electric field is applied by connecting a suitable DC power supply between negative electrode 4 and positive electrode 5. The voltage gradient generated is applied for a time period sufficient to separate the particles. If the electrophoretic mobilities of the particles are known then the time required to achieve separation can be calculated knowing the magnitude of the voltage applied. If the electrophoretic mobilities of the particles are not known the particles can be observed throughout the process through a transparent cover 3 provided on the top of the chamber. Various optical techniques known to the artisan can be used for observing the particles.

There are alternative methods for applying the electric field other than applying a DC voltage between spaced apart electrodes within the fractionation chamber. Many of these techniques are known from gel electrophoresis and would also be useful in connection with the present invention. An AC voltage can be applied between the electrodes whereby the changing polarity of the voltage causes the particles to first move in one direction and then to move in a reverse direction when the polarity changes. Typically the frequency of the AC signal is not uniform in that the time spent applying the first "positive" (or "negative") voltage is greater than the time spent applying the reversed voltage otherwise the net motion of the particles would not be in the forward direction. Another method involves employing a second pair of electrodes in the fractionation chamber for applying a voltage gradient substantially perpendicular (80°-90°) to the first voltage but still parallel to the membrane. Thus, a voltage gradient is applied using the first pair of electrodes followed by terminating this voltage and applying the second gradient using the second pair of electrodes whereby the particles begin to move at 90° to their original direction. The second gradient can then be terminated and the first gradient reapplied, and so on. This causes the particles to follow a zig-zag path and is useful for causing the faster moving particles to travel a greater distance when this is desirable for separation of the particles. In addition to applying the voltage gradients described above it can also be useful to establish a pH gradient parallel to the voltage gradient by any of the well known methods used in gel electrophoresis.

Once the particles are separated the next step depends on the purpose of the fractionation. If the purpose of the fractionation is to analyze a mixture to determine if a certain species is present one only need to observe the separated particles and identify them. This cam be achieved by using any of the well known optical or spectrophotometric methods known to the artisan. However, in some cases it may be desirable to collect the particles. This can be achieved in a variety of ways. The separated particles can be syphoned off of the membrane surface using a pipette or other suitable device. Alternatively, a removable collection tube can be provided having its opening flush with the membrane surface just before the electrode that the particles are migrating towards so that the fastest moving particles fall into the tube. New tubes can be substituted to collect the slower moving species. A more sophisticated collection method would be to discontinue the electric field used for fractionation and apply a new field perpendicular to the first field but parallel to the membrane so that the particles move with second field towards a linear array of collection tubes arranged along an edge of the membrane.

Figure 2:
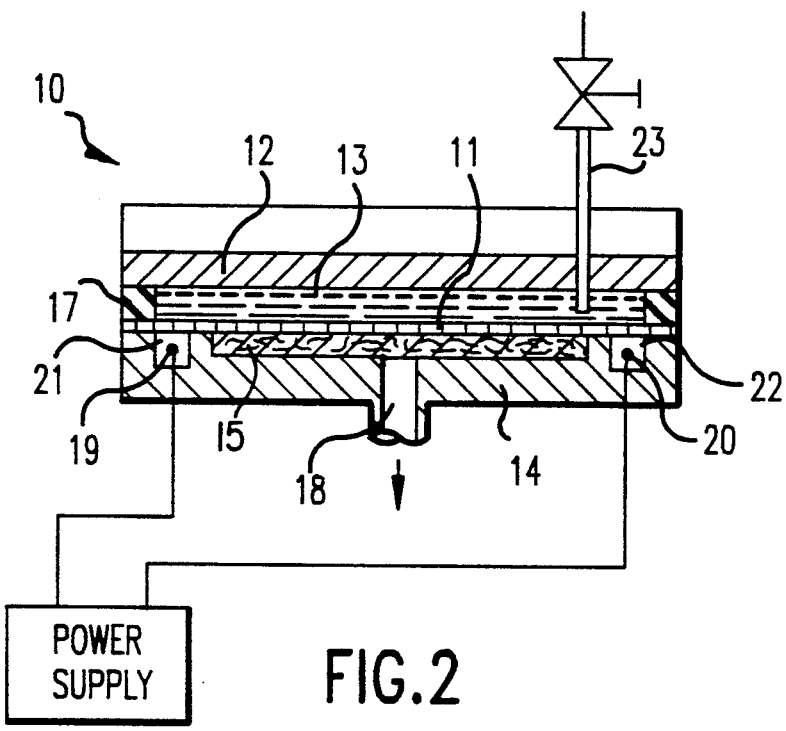
FIG. 2 is a cross-sectional view through the length dimension of a fractionation chamber.
Figure 3:
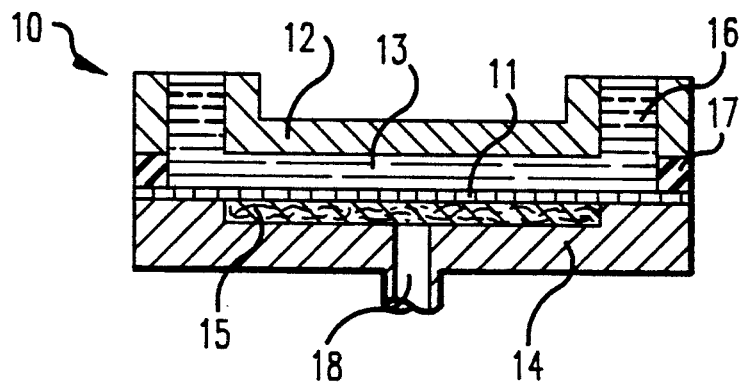
FIG. 3 is a cross sectional view through the width dimension of a fractionation chamber.

A fractionation chamber suitable for carrying out the method described above will be described with reference to FIGS. 2 and 3. Fractionation chamber 10 comprises bottom plate 14 and upper plate 12. Bottom plate 14 has depression 24 formed therein which is filled with porous support 15. At least one passageway 18 is provided in plate 14 for the outflow of electrolyte. Semipermeable membrane 11 is supported by porous support 15 and bottom plate 14. Upper plate 12 is sealed to bottom plate 14 via gasket 17. Fractionation gap 13 is created between plates 12 and 14 is filled with conductive electrolyte solution 25. Reservoirs 16 supply electrolyte 25 into gap 13 from opposite sides of chamber 1 perpendicular to the direction of fractionation so that a unidirectional flow of electrolyte across the fractionation path is minimized. To minimize leakage of current through each reservoir they may be separated from the fractionation gap 13 by suitable porous or non-porous dividers dividers (not shown).

The pressure differential across the membrane to induce flow therethrough can be applied in a number of different ways. A pump (not shown) can be included downstream of the membrane such that pumping of the electrolyte from the downstream side reduces the electrolyte pressure relative to the upstream side. Alternatively, pumping means can be included on the upstream side of the membrane to slightly pressurize the electrolyte above the membrane versus the downstream side. Another means to pressurize the electrolyte on the upstream side of the membrane is simply to locate the reservoir above the level of the fractionation chamber such that gravity causes the reservoir to exert pressure on the membrane.

Channels 21 and 22 are provided in bottom plate 14 for electrodes 19 and 20. Electrodes 19 and 20 are generally each in the form of a wire and channels 21 and 22 should have a length sufficient to accommodate the length of each electrode. To prevent leakage of by-products of any electrode reactions into fractionation gap 13 channels 21 and 22 are covered by a portion of membrane 11. Other suitable membranes may be provided to separate electrode compartments 21 and 22 from fractionation gap 13. To prevent leakage of the electrolyte 25 around the edges of each channel 21 and 22 membrane 11 can be sealed around each compartment by means of a suitable adhesive or welding. Separate electrolyte streams are recirculated through electrode channels 21 and 22 to a suitable outside reservoir by a two channel peristaltic pump (not shown) for removing by-products of the electrodes as well as Joule's heat. Other suitable heat exchange means for cooling the backside of membrane 11 may be provided in bottom plate 14.

A suitable sample introduction means 23 is provided through upper plate 12. Multiple sample introduction means could be provided so that the sample could be placed at various locations on the membrane depending on the charges of the particles as discussed above.

Semipermeable membrane 11 is preferably made from a polymeric material such as cellulose, cellulose acetate, polysulphone, polypropylene, polyethylene, polyhalohydrocarbons, polycarbonate, polyacrylonitrile, polyacrylamide and the like. Alternative but less preferred materials include ceramics such as alumina and other dielectric materials. The particular choice depends mostly on the chemical nature of the electrolyte since membrane 11 should be inert to the particular electrolyte chosen. An additional consideration is that the membrane should not absorb the particles being separated.

The pore size of the membrane should be less than the size of the particles to be separated. The range of particle sizes for which this invention is suited ranges from 0.02 microns in diameter to 100 microns. For most biological applications the particle sizes will be in the range of 0.1 microns to 40 microns. A preferred range of pore sizes for this range of particle sizes is between about 5 and 200 Angstroms. However, pore sizes may be as large as a fraction of a micron depending on the sizes of the particles being separated.

The membrane may be homogeneous but it is more convenient if the membrane is a heterogeneous asymmetric type supported on a nonwoven polymer support. The membrane thickness can range from about 5 to about 300 microns. Such thin structures require support such as provided by porous support 15 in order to withstand the pressure differential created during fractionation.

An alternative form for the membrane is a hollow fiber made from the above described materials. The fiber can have an internal diameter of from 100 microns to several millimeters. Essentially, the fiber should be large enough for the particles to fit within its diameter.

Bottom plate 14 can be made of any suitable plastic such as PVC, polyolefins, polyhalohydrocarbons, and the like, or glass. The primary concerns are that bottom plate 14 should be non-electrically conducting and should be inert toward the electrolyte used.

Upper plate 12 is preferably made from a clear plastic such as acrylic, polycarbonate, polysulfone, and the like or glass.

Porous support 15 is preferably made from a plastic screen, sintered plastic particles, or a porous ceramic material. An alternate embodiment to porous support 15 is simply to provide parallel grooves, a grid-like pattern, or other similar structures in bottom plate 14 which both support the membrane and permit the outflow of electrolyte.

A specific fractionation chamber will now be described with reference to the Figures. Bottom plate 14 is formed from a slab of polyethylene about 18 cm long, 8 cm wide and 3 cm thick. A pattern of parallel grooves are cut into the upper surface of bottom plate 14, said pattern measuring about 12 cm by 5 cm. Each groove is 0.2 cm deep and 0.1 cm wide. The grooves are in communication with an outside container for the outflow of electrolyte. Two electrode compartment channels are also cut into the upper surface of lower plate 14, one at each end of the groove pattern and parallel thereto. A platinum wire electrode 0.06 cm in diameter and 3.5 cm long is placed in each channel. A hydrophilic regenerated cellulose 5000 molecular weight cut-off YM-5 membrane (Amicon Corp., Danvers, Mass.) is placed over substantially the entire surface of bottom plate 14. A rubber gasket is placed around the periphery of the membrane, said gasket being about 0.15 cm thick and an upper plate made from polycarbonate measuring 5 cm wide, 15 cm long, and 3 cm thick is compressingly sealed to the gasket creating a fractionation gap between the upper and lower plates. A syringe is accommodated in upper plate 12 for delivering sample onto the membrane. A pressurized buffer solution is supplied from a reservoir into the fractionation gap through multiple inlets also located in upper plate 12. Two other separate electrolyte streams are recirculated by a peristaltic pump through each electrode channel. A power supply is connected between the electrodes The method of the present invention using the above described fractionation chamber is demonstrated by using a mixture of latex beads. A mixture of negatively charged black latex beads 1.104 microns in diameter and positively charged blue latex beads 5.0 microns in diameter (both from Seradyn Inc., Indianapolis, Ind.) were used. A Seamans buffer solution of pH 7 was used as the electrolyte. A sample of each type of beads is independently suspended in the buffer and their electrophoretic mobilities measured using a Model 1 Zeta-Meter (Zeta-Meter, Inc., New York, N.Y.). The results are 4.2 m-cm/volt-sec for the black beads and 0.2 m-cm/volt-sec for the blue beads.

A 0.02 ml drop of a 2 vol.% mixture of the beads is applied to the membrane surface in the form of a small circle through the syringe located in the upper plate of the fractionation chamber. The buffer solution was pressurized so as to create a 1 psi pressure drop across the membrane. The transmembrane flow of electrolyte is about 0.6 microns/sec. An electric field of 11 volt/cm is applied along he membrane surface using the two platinum electrodes and the power supply. The electrolyte is circulated through the electrode channels at a rate of about 12 ml/min. The movement of the particles is observed through the clear upper plate. A complete separation of the blue beads from the black beads is achieved. The blue beads stayed within the injection area and the black beads migrated towards the positive electrode.

The preceding description is intended to be for illustrative purposes only and is not intended to limit the scope of the invention as set forth in the following claims.

What is claimed is:

1. An electrophoretic method for fractionating a mixture of charged particles comprising:
    placing a mixture of charged particles having different electrophoretic mobilities onto a localized portion of the surface area of a membrane, which membrane does not irreversibly hold or bind with said particles, said membrane being located within a fractionation chamber containing a conductive eluent solution;
    applying a force through said membrane, said force having a magnitude sufficient to hold the particles in a region immediately adjacent to the membrane surface but not sufficient to prevent the particles from moving along the membrane surface under an applied electric field;

applying a first electric field having its primary direction parallel to the membrane surface to move said particles from said localized portion along a trajectory that is parallel to the primary direction of the field; and continuing to apply the first electric field particles are separated by migrating with the field in accordance with their electrophoretic mobilities.

2. The method of claim 1 further comprising collecting the particles after they are separated.

3. The method of claim 1 wherein the membrane is semipermeable to the conductive solution and has an average pore size smaller than the average particle size of the smallest particle in the mixture and wherein the transmembrane force is applied by creating a pressure difference between the conductive eluent solution above and below the membrane so that the pressure above the membrane is greater whereby the solution flows continuously through the membrane so long as the pressure differential is maintained.

4. The method of claim 3 further comprising removing the solution from below the membrane and resupplying solution to the fractionation chamber above the membrane.

5. The method of claim 3 wherein the pressure difference is created by pressurizing the solution above the membrane.

6. The method of claim 3 wherein the pressure difference is created by pumping solution from below the membrane whereby the solution pressure below the membrane is less than the solution pressure above the membrane.

7. The method of claim 3 wherein the particles are separated by applying a DC electric field between spaced apart electrodes located in said chamber.

8. The method of claim 3 wherein the particles are separated by applying an AC electric field between spaced apart electrodes located in said chamber; wherein the time period of the first half cycle of the field does not equal the time period of the second half cycle.

9. The method of claim 3 comprising terminating the first electric field and applying a second electric field said second field being both substantially perpendicular to the first electric field and parallel to the membrane surface to move the particles in a direction perpendicular to their original direction.

10. The method of claim 3 further comprising establishing a pH gradient parallel to the first voltage gradient.

11. A gel-free electrophoretic method for fractionating a mixture of charged particles comprising:

movably placing a mixture of charged particles having different electrophoretic mobilities onto a localized portion of the surface area of a horizontally disposed semi-permeable membrane located within a gel-free fractionation chamber containing a conductive solution;

increasing the pressure of the conductive solution above the membrane versus the conductive solution pressure below the membrane so as to induce a substantially uniform flow of solution through the membrane, said transmembrane flow being great enough to hold the particles within a region near the membrane surface but not so great so as to prevent movement of the particles along the membrane surface under an applied electric field;

applying an electric field having its primary direction parallel to and adjacent with the membrane surface to move said particles along said surface in a direction parallel with the field direction; and discontinuing the field when at least some of the particles are physically separated from the other particles, by migrating with the field in accordance with their electrophoretic mobilities.

* * * * *